(12) United States Patent
Vaccaro

(10) Patent No.: US 11,810,657 B2
(45) Date of Patent: *Nov. 7, 2023

(54) SYSTEM AND METHOD FOR TRACKING PATIENT RECOVERY FOLLOWING ORTHOPEDIC PROCEDURE

(71) Applicant: AVKN Patient-Driven Care, LLC, Gladwyne, PA (US)

(72) Inventor: Alexander R. Vaccaro, Philadelphia, PA (US)

(73) Assignee: AVKN PATIENT-DRIVEN CARE, INC., Gladwyne, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/738,481

(22) Filed: May 6, 2022

(65) Prior Publication Data
US 2022/0262492 A1    Aug. 18, 2022

Related U.S. Application Data

(63) Continuation of application No. 16/033,806, filed on Jul. 12, 2018, now Pat. No. 11,328,806.

(60) Provisional application No. 62/533,446, filed on Jul. 17, 2017.

(51) Int. Cl.
*G16H 20/30* (2018.01)
*G16H 10/20* (2018.01)
(Continued)

(52) U.S. Cl.
CPC .......... *G16H 20/30* (2018.01); *A61B 5/1118* (2013.01); *A61B 5/4833* (2013.01);
(Continued)

(58) Field of Classification Search
CPC ......... G16H 20/30; G16H 10/20; G16H 10/60
See application file for complete search history.

(56) References Cited

U.S. PATENT DOCUMENTS

2008/0140371 A1* 6/2008 Warner ............... G16H 20/40
703/11
2009/0105550 A1 4/2009 Rothman et al.
(Continued)

OTHER PUBLICATIONS

Qin et al., "A smart phone based gait monitor system." Bodynets 2015, Sep. 28-30, 2015, Syndey, Australia, Copyright © 2015 ICST, 7 pages.

(Continued)

*Primary Examiner* — Evangeline Barr
(74) *Attorney, Agent, or Firm* — Panitch Schwarze Belisario & Nadel LLP

(57) ABSTRACT

An apparatus and method are provided that tracks patient recovery following an orthopedic procedure. A statistical computing engine implements a predictive model of the patient's post-procedural state for the orthopedic procedure based on a database of patient demographic data, comorbidities, pre-procedural walking parameters, including steps taken, and the orthopedic procedure that the patient is undergoing. The pre-procedural walking parameters are populated from physical sensor data automatically collected from the patient. The predictive model uses machine learning and is trained using training data sets. The predictive model creates a temporal trendline of post-procedural walking parameters, including steps taken, and a temporal trendline of post-procedural pain level. A processor then compares the patient's actual post-procedural state to the predictive model of the patient's post-procedural state. The post-procedural walking parameters are also obtained from the physical sensor.

20 Claims, 14 Drawing Sheets

(51) Int. Cl.
  *A61B 5/11*    (2006.01)
  *G16H 10/60*   (2018.01)
  *G16H 80/00*   (2018.01)
  *A61B 5/00*    (2006.01)
  *G16H 40/63*   (2018.01)
  *G16H 50/30*   (2018.01)
  *G16H 50/70*   (2018.01)

(52) U.S. Cl.
  CPC ........... *A61B 5/7275* (2013.01); *G16H 10/20* (2018.01); *G16H 10/60* (2018.01); *G16H 40/63* (2018.01); *G16H 50/30* (2018.01); *G16H 50/70* (2018.01); *A61B 5/1112* (2013.01); *A61B 2505/09* (2013.01); *G16H 80/00* (2018.01)

(56) References Cited

U.S. PATENT DOCUMENTS

2016/0001131 A1    1/2016  Radecka et al.
2016/0338685 A1*  11/2016  Nawana ................. G16H 40/40
2019/0147128 A1*   5/2019  O'Connor ............... G06T 17/00
                                                        703/11

OTHER PUBLICATIONS

User Guide for "ActiGraph GT9X Link + ActiLife." ActiGraph, LLC, released Nov. 28, 2017, 16 pages.
User Manual for "CentrePoint Data Hub." ActiGraph, LLC, released Jul. 11, 2017, 14 pages.

* cited by examiner

202

| ID | DOB | Sex | Zip Code | Smoking Status | Height | Weight | ... |
|---|---|---|---|---|---|---|---|
| 1002359 | 1/1/1970 | M | 19145 | Current | 70 | 170 | |
| 2234009 | 4/2/1965 | M | 49503 | Non | 72 | 240 | |
| 4564210 | 3/2/1980 | F | 23076 | Non | 63 | 145 | |

| ID | Acute or Chronic Wound | AIDS/HIV | Anemia | Asthma | Anxiety Disorder | AICD/Pacemaker |
|---|---|---|---|---|---|---|
| 1002359 | 0 | 0 | 0 | 1 | 0 | 0 |
| 2234009 | 0 | 0 | 1 | 0 | 0 | 0 |

| ID | Date | Intensity Points | steps | Calories | Active Calories | Miles |
|---|---|---|---|---|---|---|
| 1423099 | 2/16/2018 | 1297.6 | 12534 | 2024 | 337 | 4.5 |
| 1423099 | 2/17/2018 | 1352.8 | 12734 | 2043 | 393 | 4.4 |
| 1423099 | 2/18/2018 | 1151.2 | 11172 | 1972 | 334 | 3.9 |

Figure 2C

| ID | Date of procedure | Facility | Physician | ICD10 | CPT | Revision | Multi-stage | Implant | Anesthesia | ASA | ... |
|---|---|---|---|---|---|---|---|---|---|---|---|
| 1002359 | 1/1/2018 | X Hospital | Joe Smith | M17.11 | 27447 | 0 | 0 | Zimmer Vanguard | peripheral nerve blockade | II | |
| 2234009 | 2/4/2018 | Y Hospital | Jane Smith | M51.26, M54.16 | 63047 | 1 | 0 | NA | regional | II | |
| ... | | | | | | | | | | | |

| Data Source | Data Field | Patient Data |
|---|---|---|
| EMR | Age | 45 |
| EMR | Gender (1=M, 0=F) | 0 |
| EMR | BMI | 35 |
| EMR | Smoker (1=Y) | 0 |
| EMR | Former Smoker (1=Y) | 0 |
| EMR | Hypertension | 1 |
| EMR | Diabetes | 0 |
| EMR | Diagnosis | Cervical Myelopathy |
| EMR | Procedure | 2-Level ACDF |
| EMR | Facility Type | Teaching Hospital |
| Physical Sensor | Median daily steps | 1700 |
| Patient Interface | Median daily pain | 8 |

Figure 3

SYSTEM AND METHOD FOR TRACKING PATIENT RECOVERY FOLLOWING ORTHOPEDIC PROCEDURE

CROSS-REFERENCE TO RELATED APPLICATION

This application is a continuation of copending U.S. application Ser. No. 16/033,806 filed Jul. 12, 2018, the disclosure of which is hereby incorporated by reference in its entirety.

This application claims the benefit of U.S. Patent Application No. 62/533,446, filed Jul. 17, 2017, the disclosure of which is hereby incorporated herein by reference in its entirety.

COPYRIGHT NOTICE AND AUTHORIZATION

Portions of the documentation in this patent document contain material that is subject to copyright protection. The copyright owner has no objection to the facsimile reproduction by anyone of the patent document or the patent disclosure as it appears in the Patent and Trademark Office file or records, but otherwise reserves all copyright rights whatsoever.

BACKGROUND OF THE INVENTION

When patients undergo medical procedures, such as an orthopedic procedure, the medical industry typically relies upon standardized recovery protocols which are used for gauging whether a patient is on track during recovery, and for scheduling dates and frequency of appointments. For orthopedic procedures, two important recovery factors are walking parameters and level of pain. Many factors dictate the likely recovery path, including the patient's pre-surgical state. The reliance upon standardized recovery protocols may result in overestimating or underestimating a particular patient's recovery path, which, in turn, may result in providing too little or too much (i.e., unnecessary) post-surgical treatment. Furthermore, the current industry practice of relying upon self-reporting of pre-surgical and post-surgical walking parameters further complicates the ability to accurately gauge whether a patient is recovering as expected.

Accordingly, what is needed is a system that more accurately predicts a patient's recovery process, particularly, with respect to walking parameters and level of pain, and which relies upon automated, objective measurements of pre-surgical and post-surgical walking parameters. The present invention fulfills such a need.

SUMMARY OF THE INVENTION

An apparatus tracks patient recovery following an orthopedic procedure. A statistical computing engine implements a predictive model of the patient's post-procedural state for the orthopedic procedure based on a database of patient demographic data, comorbidities, pre-procedural walking parameters, including steps taken, and the orthopedic procedure that the patient is undergoing. The pre-procedural walking parameters are populated from physical sensor data automatically collected from the patient. The predictive model creates a temporal trendline of post-procedural walking parameters, including steps taken, and a temporal trendline of post-procedural pain level. A processor then compares the patient's actual post-procedural state to the predictive model of the patient's post-procedural state. The post-procedural walking parameters are also obtained from the physical sensor.

BRIEF DESCRIPTION OF THE DRAWINGS

FIGS. 2A-2D are data tables for use in the system of FIG. 1;

FIG. 3 shows sample patient data for use in a predictive model used in the system of FIG. 1;

DETAILED DESCRIPTION OF THE INVENTION

Certain terminology is used herein for convenience only and is not to be taken as a limitation on the present invention. The words "a" and "an", as used in the claims and in the corresponding portions of the specification, mean "at least one."

This patent application includes an Appendix having a file named appendix688464-17U2.txt, created on May 5, 2022 and having a size of 1,789 bytes. The Appendix is incorporated by reference into the present patent application. One preferred embodiment of the present invention is implemented via the source code in the Appendix. The Appendix is subject to the "Copyright Notice and Authorization" stated above.

PART 1: System for Tracking Patient Recovery Following an Orthopedic Procedure

I. Overview

Figure 1:
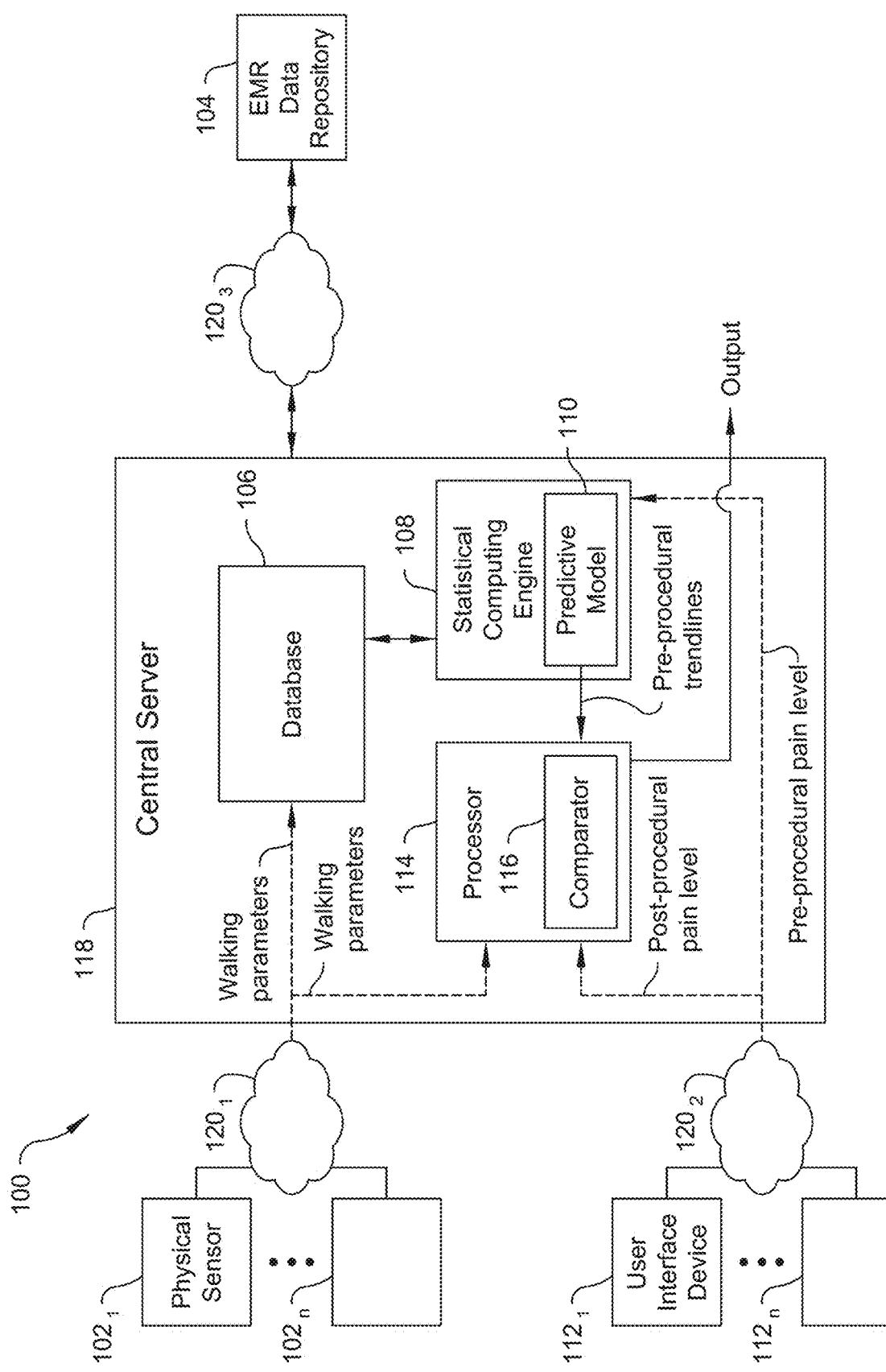
FIG. 1 is a schematic diagram of a system for tracking patient recovery following an orthopedic procedure in accordance with one preferred embodiment of the present invention.

FIG. 1 is a schematic diagram of an apparatus (system 100) for tracking patient recovery following an orthopedic (orthopaedic) procedure. The system 100 includes a physical sensor 102 configured to collect pre-procedural and post-procedural walking parameters, including steps taken, and an electronic medical record (EMR) data repository 104, including EMR data for the patient undergoing the orthopedic procedure. The EMR data repository 104 includes electronic health records (EHRs). An EMR data repository or "EMR system" is a narrower view of a patient's medical history, while an EHR data repository or "EHR system" may contain more comprehensive data of the patient's overall health, since some types of health-related data is not necessarily medical-related data. However, in many instances, the terms "EMR system" and "EHR system" are used interchangeably.

The system 100 also includes a database 106 in electronic communication with the physical sensor 102 and the EMR data repository 104. The database 106 includes at least patient demographic data (e.g., one or more of patient age, BMI, and gender) obtained from the EMR data repository 104, comorbidities, pre-procedural walking parameters, including steps taken, and the orthopedic procedure that the patient is undergoing. The pre-procedural walking parameters are obtained from the physical sensor 102. FIG. 1 shows physical sensors $102_1$-$102_n$ which represent sensors for a plurality of patients.

The system 100 further includes a user interface device 112 configured to temporally allow the patient to electronically communicate their pre-procedural pain level and post-procedural pain level.

The system 100 further includes a statistical computing engine 108 in communication with the database 106 and the user interface device 112, and is configured to use the above-identified items of the database 106 and the pre-procedural pain level data collected by the user interface 112 to implement a predictive model 110 of the patient's post-procedural state for the orthopedic procedure. The predictive model 110 creates at least a temporal trendline of post-procedural walking parameters, including steps taken, and a temporal trendline of post-procedural pain level. FIG. 1 shows user interface devices $112_1$-$112_n$ which represent user interface devices used by a plurality of different patients.

The system 100 further includes a processor 114 having a comparator 116 configured to compare the patient's actual post-procedural state to the predictive model 110 of the patient's post-procedural state. The processor 114 is in electronic communication with the statistical computing engine 108, the physical sensor 102 and the user interface device 112. The comparator 116 of the processor 114 temporally compares the post-procedural walking parameters, including steps taken, to the temporal trendline of post-procedural walking parameters, including steps taken. The comparator 116 of the processor also temporally compares the post-procedural pain level to the temporal trendline of post-procedural pain level. The comparator 116 of the processor 114 further outputs the results of the comparison.

In addition to steps taken, the physical sensor 102 may also be configured to collect other types of pre-procedural and post-procedural walking parameters, such as walking velocity, gait cadence, and distance of continuous walking. Additional temporal trendlines may be created for one or more of these other walking parameters, both pre-procedural and post-procedural, and which can then be compared to one another in the same manner as the walking steps trendlines.

In one preferred embodiment, the physical sensor 102 is a mobile device (e.g., smartphone/mobile phone) that includes a movement/motion sensor (e.g., accelerometer), and an application configured to receive data from the sensor.

In another preferred embodiment, the physical sensor 102 includes a device worn by the patient and configured to collect movement/motion data, and a mobile device (e.g., smartphone) including an application configured to receive data from the device. One example of such a device is an epidermally attached data device (e.g., device shown in FIG. 7B, as described below).

The database 106, statistical computing engine 108, and processor 114 are preferably all housed within a central server 118. The central server 118 is in communication with the physical sensor 102, user interface device 112 and EMR data repository 104 via electronic networks $120_1$-$120_3$, such as the Internet. The database 106, statistical computing engine 108, and processor 114 may alternatively be located in different servers that communicate with each other via additional electronic networks 120.

II. Detailed Disclosure

A. EMR Data Repository

As described above, demographic data is retrieved from the patient's EMR data repository 104 and communicated to the database 106. Commercially available EMR data repositories that are suitable for use with the present invention include Epic® (Epic Systems Corporation) and eClinical Works® (eCW). An EMR agnostic platform, such as Informed Mindset Medical, may act as a third party in the data transfer from the EMR data repository 104 to the database 106, thereby reducing the burden to customize queries for the myriad of EMR systems on the market today.

B. Database 106

FIGS. 2A-2D show examples of data tables of the database 106. FIG. 2A shows a data table 202 of the demographic data retrieved from the EMR data repository 104 for selected patients identified by the ID field. FIG. 2B shows a data table 204 of comorbidities for selected patients identified by the ID field. The comorbidities are coded as a "0" (disease or condition does not exist) or a "1" disease or condition exists.

FIG. 2C shows a data table 206 selected pre-procedural walking parameters of a sample patient for consecutive dates, including steps taken. FIG. 2D shows a data table 208 of the orthopedic procedure that selected patients are undergoing, and selected data related to their procedures.

C. Statistical Computing Engine

As discussed above, the statistical computing engine 108 uses a predictive model 110 to create at least a temporal trendline of post-procedural walking parameters, including steps taken, and a temporal trendline of post-procedural pain level.

To create a post-procedural temporal trendline of the number of steps taken, a mixed model is created from historical patient data. Specifically, a mixed-effect linear regression model is built to predict daily step count, controlling for the variables collected prior to the procedure, including: two-week median daily step count, age at time of procedure, sex, BMI, smoking status, comorbid conditions, diagnosis, procedure, procedure facility. Imputation procedures are implemented to complete missing predictors and post-procedural data. The model is constructed using a random subset of all available subject data and tested against an independent subject sample in order to provide patients and physicians an estimate of the model accuracy. As additional patient data is collected by the apparatus, the new data is added to the training and test sets. Machine learning approaches are applied to continuously tune the mixed models, or to train new types of predictive models, including classifiers.

Figure 4A:
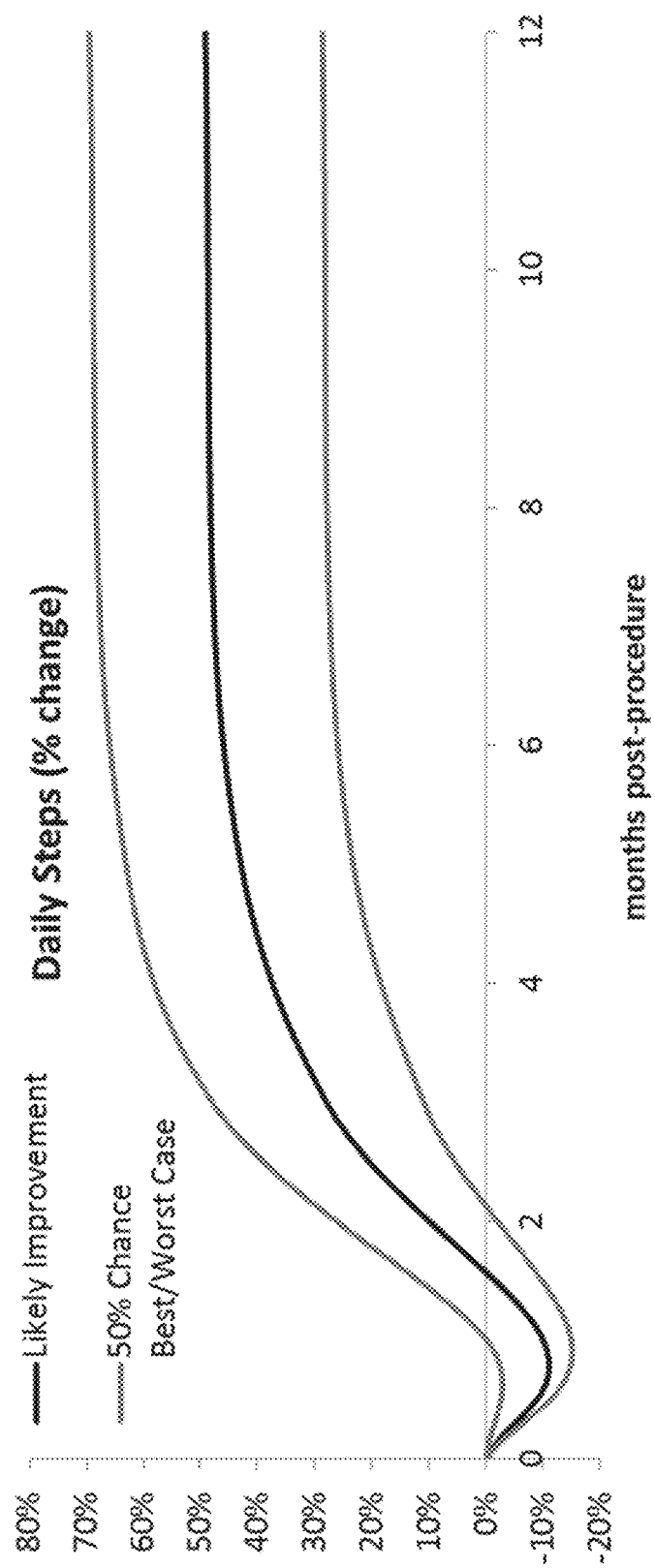
FIGS. 4A, 4B, 5A, and 5B are temporal trendlines generated by the system of FIG. 1.
Figure 4B:
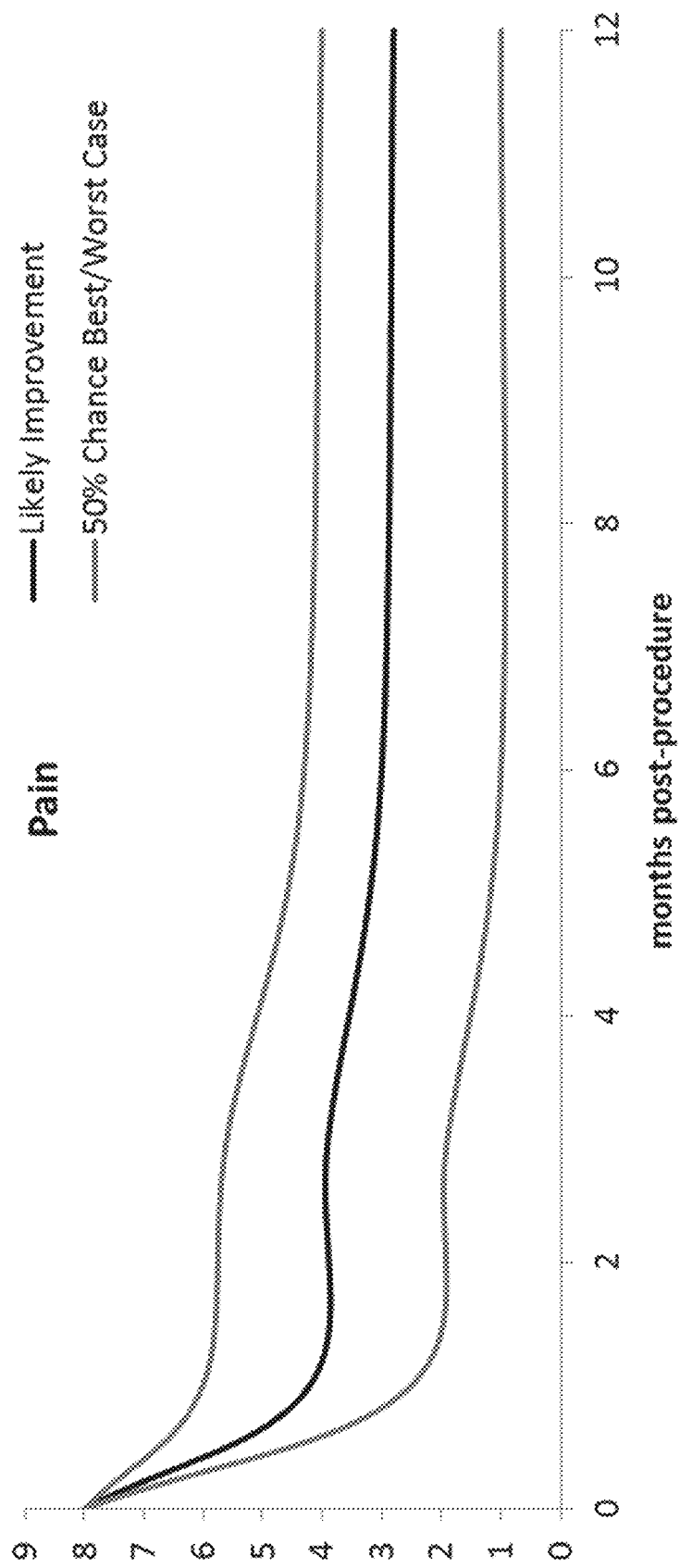

Consider the following example for a specific patient having patient data shown in FIG. 3. Based on this set of patient data, the predictive model 110 generates two post-procedural temporal trendlines, shown in FIG. 4A (temporal trendline of post-procedural steps taken), and FIG. 4B (temporal trendline of post-procedural pain level). The dark line in FIG. 4A illustrates the anticipated percent increase in daily steps taken over the median daily steps taken prior to the procedure, as shown in FIG. 3. The dark line in FIG. 4B illustrates the expected pain reported, given the median daily pain level reported prior to the procedure, as shown in FIG. 3. The gray lines in FIGS. 4A and 4B bound the range within which 50% of patients are expected to fall within.

One suitable programming language for implementing the statistical computing engine 108 is "R" which is supported by the R Foundation for Statistical Computing. The source code provided in the Appendix demonstrates construction of a mixed-effect linear regression model and random forest model. The mixed-effect regression in this example assumes a random intercept for subjects ("id") to predict "outcome" at multiple post-operative time-points. For this example, it is assumed that the independent variables of interest have already been identified. Conversely, in the random forest model example, recursive feature selection first ranks the most important variables. The n most important features are selected for inclusion in the model. For both the mixed-effect regression model and random forest model, model performance is tested against a separate, independent sample ("test.data"); that same code also generates predictions for new patient data collected by the apparatus.

D. User Interface Device

The user interface device 112 may be any device suitable for electronically receiving input data regarding the patient's pain level and electronically communicating that data to a remote location, here, statistical computing engine 108 for the pre-procedural pain level and the processor 114 from the post-procedural pain level.

In one embodiment, the user interface device 112 is a user's mobile device, such as a smartphone. The smartphone example may be implemented by prompts sent to the smartphone via short message service protocol (SMS; text message). An example of the prompt and response is as follows:

[Name], how would you rate the average pain associated with your right knee today? From 0 (no pain) to 10 (worst imaginable pain)?
User: 3
SMS prompt: You entered 3, is this correct? Type Y to confirm, N to change your answer
User: Y
SMS prompt: Thank you!

In another method, the user may be prompted via a smartphone app. Such a prompt may use a similar script as the SMS protocol using a chatbot built on the Azure Bot Service platform, commercially available from Microsoft® Corporation.

The user interface device 112 may also be configured to encourage patient engagement by employing gamification techniques. (Gamification is the application of game-design elements and game principles in non-game contexts.) Gamification techniques include:

(i) personalized prompts with feedback of recent input and progress status,
(ii) provide information that a specific user values to incentivize engagement One example of a message prompt to encourage user engagement is:

"Your pain has been holding steady these last few days, but you have only completed 4 entries this past week. It's still good to maintain the habit of monitoring the pain intensity. How would you describe the pain associated with your right hip today?"

Information provided to the user includes general health-related information as well as non-health related information that is related to user interests (e.g., history, stamps, geography). For a patient interested in reading about the latest research related to their condition, an example prompt may be:

Did you know that recent research suggests that biomarkers from routine urine samples may predict the occurrence of osteolysis after hip replacement?
Click here to read more Upon opening the smartphone app, users are automatically asked to select a numeric value to describe their pain intensity.

For a patient who is interested in stamp collecting, an example prompt may be:

USPS Scooby-Dooms Forever stamps are being issued today.
Click here to read about the initiative associated with these stamps.

Upon opening the smartphone app, users are automatically asked to select a numeric value to describe their pain intensity.

The feedback that users receive after the procedure is also an example of gamification. In return for engaging with the user interface and for reporting walking parameters, users receive feedback on post-procedural progress.

E. Processor and Comparator

As discussed above, the comparator 116 of the processor 114 temporally compares the patient's actual post-procedural state to the predictive model of the patient's post-procedural state and outputs the results of the comparison. In one preferred embodiment, the comparison is shown as another line on the temporal trendline graphs of FIGS. 4A and 4B. See, the dot-dash lines in FIGS. 5A and 5B.

Figure 5A:
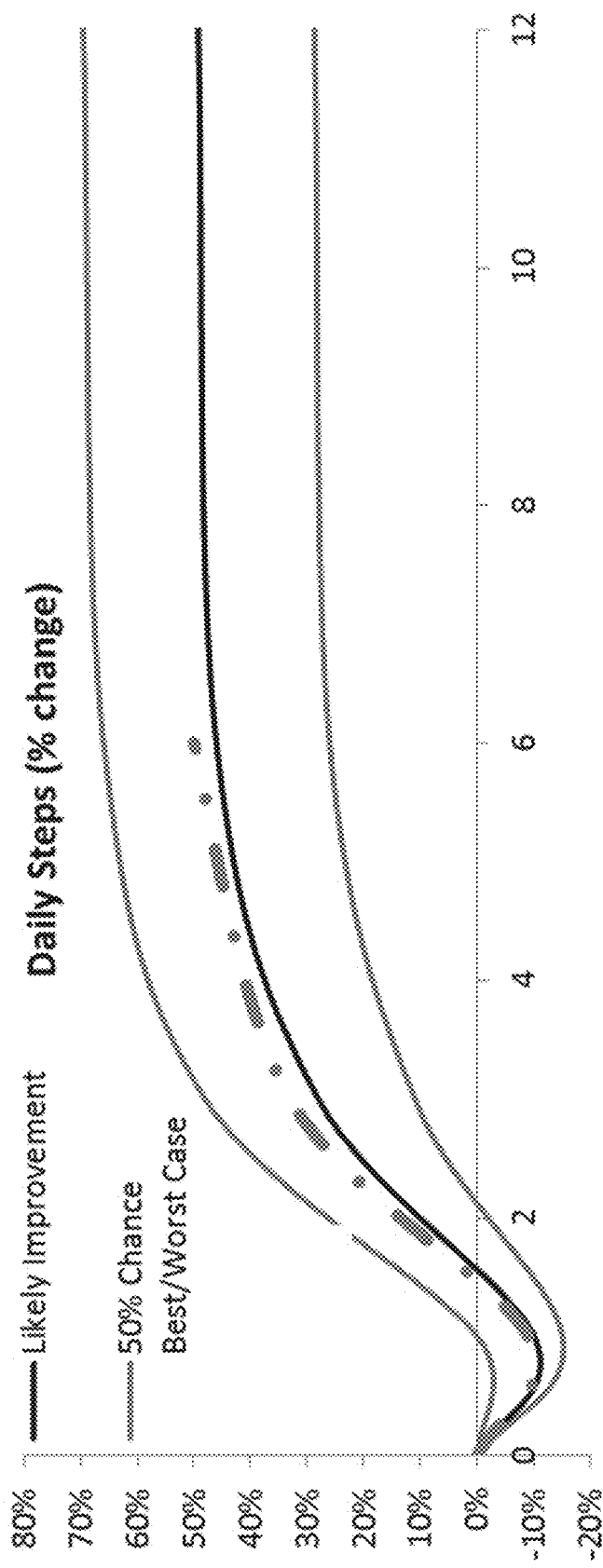
Figure 5B:
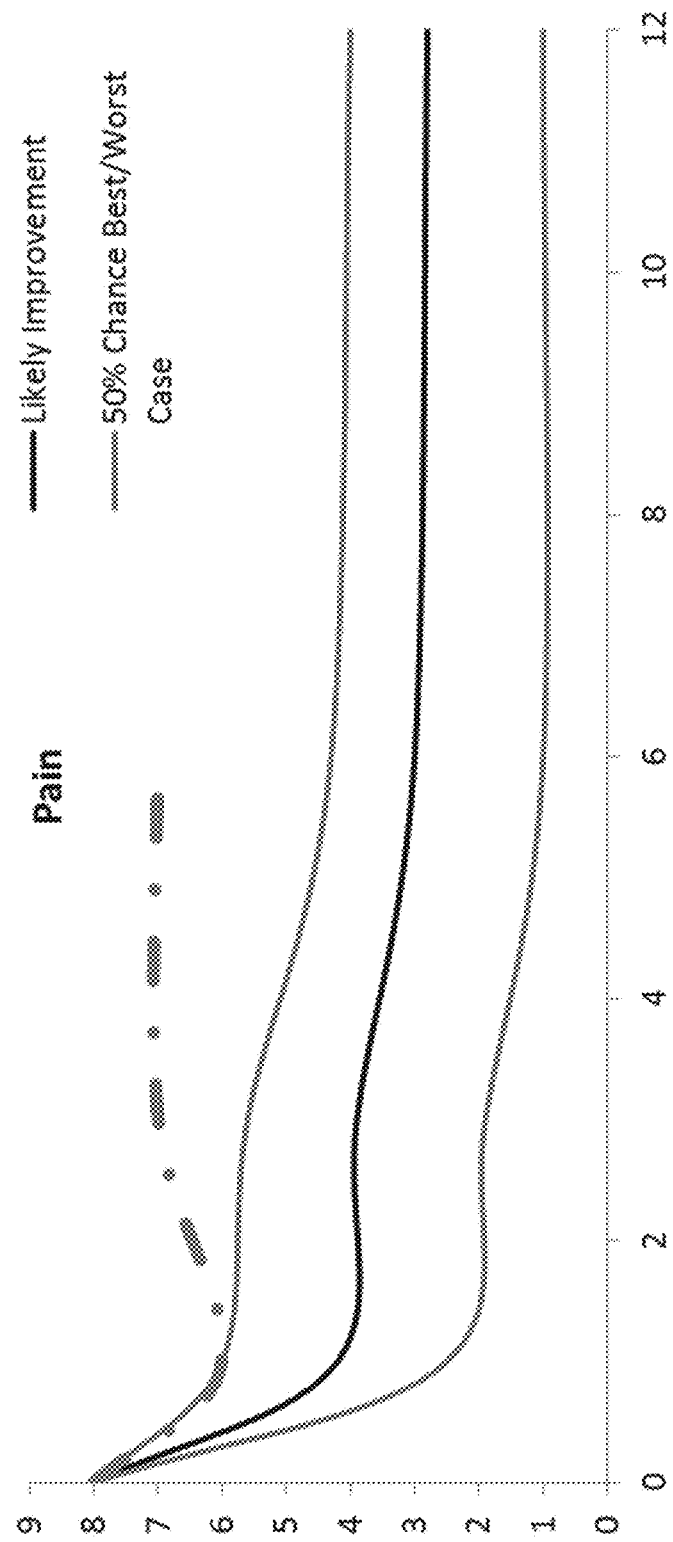
Figure 6:
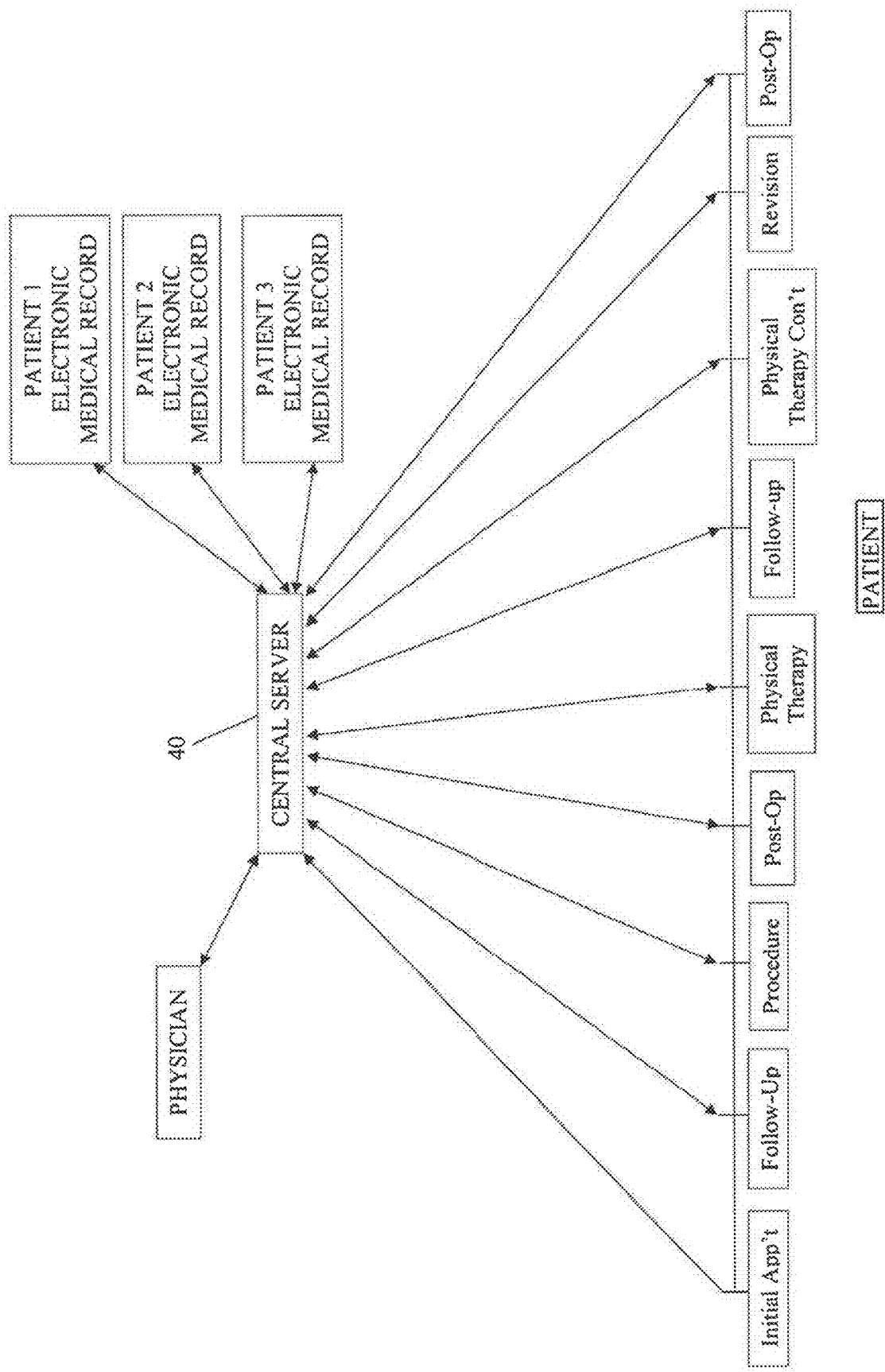
FIG. 6 is a block diagram and timeline of a system for sending and receiving patient information during a period of time from a patient's initial appointment with a physician through post-op or post-procedure, and for integration of subjective and objective outcome measurement in orthopedics in accordance with another preferred embodiment of the present invention.

In the example of FIGS. 5A and 5B, 6 months after 2-level Anterior Cervical Discectomy and Fusion (ACDF) procedure to treat cervical myelopathy, the patient's daily step count is near the predicted value and within the bounds that 50% of patients will be in. However, pain reported by the patient remains high, and is, in fact, in the top 15%. This condition results in sending prompts to both the patient and the physician. The patient is prompted via SMS or a mobile app to reach out to their medical provider. The medical provider is prompted via SMS or a physician user interface to review the patient's chart, and, if necessary, have a member of the staff contact the patient. Using this information and any additional information provided by the patient via the follow-up contact, the provider may decide to bring the patient in for an office visit to evaluate the source of the pain or refer the patient to another specialist. If the patient's reported pain fell within the 50% bounds, no such alerting would necessarily occur. Similar alerts may be programmed to be sent to the patient and the medical provider if the patient's daily step count is outside of the 50% bounds.

Other actions may be taken based on the results of the comparison performed in the comparator 116 of the processor 114, such as automatically modifying post-surgical appointment schedules. In the example of FIG. 5B, the next patient appointment may be accelerated or more frequent appointments may be scheduled.

F. Physical Sensor

The physical sensor 102 may be any sensor configured to collect walking parameters, including steps taken. One device that collects step count data and which is suitable for use in the present invention is ActiGraph GT9X Link, commercially available from ActiGraph, LLC, Pensacola, Fla. This device is a research grade sensor equipped with a 3-axis accelerometer and inertial motion unit (IMU) sensors. This device may also communicate to a data hub, such as the ActiGraph CentrePoint Data Hub, via USB 2.0 or Bluetooth®. The CentrePoint Data Hub is a home-based communication gateway that securely transmits data captured by ActiGraph activity monitors to the CentrePoint cloud software platform via 3G cellular network, which, in turn, allows the data to be provided to the database 106 and the processor 114. No personal computer or smartphone is required for implementing this embodiment.

In another embodiment, the physical sensor 102 is self-contained within a smartphone. For example, the Apple® iPhone® includes a motion coprocessor which gathers data from accelerometers, gyroscopes and compasses within the iPhone to measure motion and fitness data such as body motion, step count, and stairs climbed. Steps data is available from the built-in Apple Health app. Similar integrated smartphone sensors are also packaged in Android-based smartphones, such as the Samsung® Galaxy® S9 and walking parameters, such as step count, can be captured and tracked using a downloadable app such as Google Fit. Apple Health Records application programming interface (API) and Google Fit APIs allow the data to be provided to the database 106 and the processor 114.

In yet another embodiment, the physical sensor 102 includes a device worn by the patient and configured to collect movement/motion data, including step count, and a mobile device including an application configured to receive data from the device. One such configuration includes a sensor, such as a Fitbit® (e.g., Fitbit Charge™), which uploads data to the cloud via the Fitbit mobile app executing on the patient's smartphone. That is, data from the Fitbit is communicated to the smartphone via Bluetooth, and the Fitbit mobile app executing on the smartphone calculates the walking parameters, such as the step count. The Fitbit app may then upload this data to the cloud. Fit provides a web API that enables third-party applications to access and write data on behalf of users so that the walking parameters may be provided to the database 106 and the processor 114.

Figure 7A:
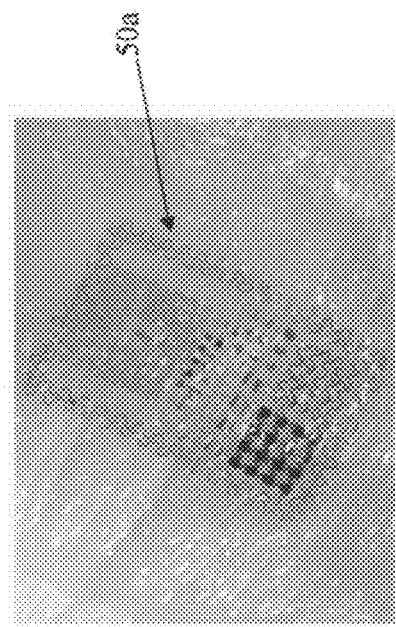
FIG. 7A is a schematic diagram of a sensor system that may be utilized with the system of FIG. 6.
Figure 7B:
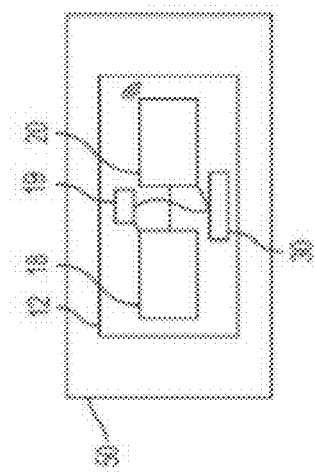
FIG. 7B is a top plan view of a sensor system that may be utilized with the system of FIG. 6.

In yet another embodiment, the physical sensor 102 is an epidermally attached data device, as shown in FIG. 7B and described in more detail below.

G. Patient-Reported Outcome Measures (PROMs)

The user interface device 112 may also be configured to temporally collect both static and computer-adaptive patient-reported outcome measures (PROMs); In particular, patients are prompted to complete measures developed by the Patient-Reported Outcomes Measurement Information System (PROMIS®) including the Global Health 10 and the computer-adaptive physical function surveys. Patients may also be prompted to complete legacy health-related quality of life (HRQoL) outcomes and disease- and symptom-specific outcome measures. Examples of HRQoL measures include the SF-12, VR-12, and EQ5D. Examples of disease- and symptom-specific measures include the Neck Disability Index, Foot and Ankle Ability Measure, Knee injury and Osteoarthritis Outcome Score, Hip disability and Osteoarthritis Outcome Score, and the Disabilities of the Arm, Shoulder and Hand.

H. Myelopathy (Compression on Spinal Cord) Example

In one example, a spine orthopaedic surgeon identifies a patient as an appropriate candidate for surgery to treat cervical myelopathy at C6-C7. Typically, patients are scheduled for surgery at 3-4 weeks out, allowing time for the patient to obtain appropriate clearances (e.g., cardiology) and pre-admission testing. A patient account is created in the system 100, allowing health data to be pulled from the patient's EMR. The patient is provided with instructions for enabling the patient interface (user interface device 112) in order to collect and transmit data to the central server 118. In this example, the physical sensor 102 is integrated with a patient's Samsung Galaxy J7. After two weeks of walking parameters are collected, the statistical computing engine 108 computes the predicted timeline of patient outcomes for walking parameters and pain, and shares them with the patient and care provider. The system 100 continues to collect the patient's walking parameters and pain input after the procedure, providing the patient and care provider with comparative data between what is actually reported and what was predicted. The patient and care provider are also provided with a numerical value that represents the percentage of patients that typically report better (or worse) walking parameters and pain.

An alternative workflow is patient-initiated, whereby a patient with orthopaedic-related pain downloads the user interface to the mobile phone. The patient tracks the walking parameters and pain. If the patient decides to then see an orthopaedic clinician and that orthopaedic clinician enables the system 100 to communicate with the EMR data repository 104, all baseline data is available to create the temporal predictions for the patient, which could be part of the shared-decision making process when identifying patient treatment options.

I. Other Walking Parameters

The detailed examples described above generate pre-surgical and post-surgical trendlines for the walking parameter of "steps taken." However, similar trendlines may be created for other walking parameters, such as walking velocity, gait cadence, and distance of continuous walking, using the same techniques described above for "steps taken." The physical sensor 102 must be capable of collecting the raw data to calculate these walking parameters. Sensors exist today for measuring all of these walking parameters. Gait analysis sensors are known and can be used for determining gait cadence. Furthermore, raw data obtained from some of the commercial sensors described above can be used for calculating some of these walking parameter, such as walking velocity and distance of continuous walking.

Part 2: System and Method for Integration of Subjective and Objective Outcome Measurement in Orthopedics I. Background of the Invention (Part 2)

It is known to track and manage patient medical information utilizing electronic medical records ("EMR"). These records can be utilized to provide diagnostic information to a treating physician and the patient's history of information can be utilized to measure outcomes, eliminate potential diagnoses or point toward potential diagnoses.

Subjective medical forms are often used to collect data and information regarding a patient's current health, symptoms, conditions and patient related outcomes ("PRO"). The forms are typically provided to a patient during each appointment or procedure with their physician and are also often provided electronically following and between appointments or procedures. Compliance with completion of these subjective medical forms is relatively high, often greater than 90% during an appointment or procedures with the patient's physician, but is often relatively low, less than 40%, between and following appointments and procedures. Such low compliance with patient outcome reporting can have a negative impact on best practices for procedures and follow-up treatments, such as physical therapy or other related therapies associated with the patient's diagnosis or the procedure associated with the patient. The low compliance with PRO reporting between visits can also lead to undesirable and undetected complications for patients, such as infections, setbacks and expensive emergency room treatment.

It is desirable to design, develop and employ a system and method to incorporate objective information related to the patient in combination with the subjective information and increase compliance with reporting of the patient's condition following procedures and between appointments and procedures. It is also desirable to design, develop and employ a system and method that encourages a patient's compliance with between appointment subjective medical forms, prescribed therapies, such as physical therapy, post-acute recovery, and objective information related to the patient's condition, such as movement, compliance with physical therapy, range of motion and other related objective information associated with the patient.

There are situations where it is desirable to record and save daily activity (e.g. walking, running, sitting, pain scale, etc.) of a patient between appointments with a physician and between or following medical procedures. Accurate tracking of such information could reduce the number of required appointments for the patient, thereby reducing overall healthcare costs and burden on the patient. Data relating to a patient's activity is a good indication of the patient's physical condition, abilities at a certain time and recovery when considered over time during a patient's recovery, particularly for recovery from orthopedic procedures, such as total hip and knee replacements or other extremity procedure. Tracking the patient's movement can be invaluable in the diagnosis and treatment of such recovery and in the general monitoring and maintenance of the patient's health and well-being. Access to data relating to a subject's daily activity and other physical conditions allows for better supervision of a subject's adherence to instructions or a treatment plan, such as compliance and progress with physical therapy and general ambulation following hip or knee replacement or other orthopedic procedures.

Subjective forms that are filled-out by the patient between physician visits and procedures are often utilized to log and record the patient's progress and daily activities following procedures. Compliance with these forms and questionnaires is relatively low, particularly when the patient is recovering successfully. As the data received from such subjective forms and questionnaires are subjective and typically received from only a small portion of the potential patients, normalized universal standards are hard to establish.

A hybrid system and method that combines subjective forms with objective data acquisition to consistently track a patient's well-being is, therefore, desirable to continue tracking of the patient's progress following procedures, particularly when their recovery is progressing normally or ahead of schedule and the tendency of the patient is to discontinue compliance with subjective forms. The preferred system addresses the shortcomings of these described prior art systems by combining subjective an objective data acquisition and utilizing the acquired data to decrease healthcare costs and improve patient outcomes.

II. Brief Summary of the Invention (Part 2)

Briefly stated, the preferred invention is directed to a system for tracking patient recovery following an orthopedic procedure conducted by a physician utilizing subjective data and objective data and considering the patient's electronic medical record. The system includes a central server configured to receive the subjective and objective data and transmit messages to and from the patient and to and from the physician. A data collection tool is associated with the patient. The data collection tool is configured to receive questionnaires from the central server and prompt the patient to provide answers to the questionnaires at a predetermined time following the orthopedic procedure. The answers to the questionnaires comprise at least a portion of the subjective data. The data collection tool is also configured to sense location data of the patient following the procedure. The location data comprises at least a portion of the objective data. The data collection tool is configured to transmit the answers and the location data to the central server. The central server creates a risk profile of the patient based on the electronic medical records. The central server compiles the risk profile, the subjective data and the objective data and transmits a series of physician appointments to the data collection tool based on the compilation.

III. Detailed Description of the Invention (Part 2)

Certain terminology is used in the following description for convenience only and is not limiting. Unless specifically set forth herein, the terms "a", "an" and "the" are not limited to one element but instead should be read as meaning "at least one". The words "right," "left," "lower," and "upper" designate directions in the drawings to which reference is made. The words "inwardly" or "distally" and "outwardly" or "proximally" refer to directions toward and away from, respectively, the geometric center or orientation of the device, systems and instruments and related parts thereof. The terminology includes the above-listed words, derivatives thereof and words of similar import.

It should also be understood that the terms "about," "approximately," "generally," "substantially" and like terms, used herein when referring to a dimension or characteristic of a component of the invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

Referring to FIG. 6, data and information related to patients receiving treatment is collected, stored and analyzed during the course of the patient's treatment. The patient's medical history is typically stored in an electronic medical record ("EMR"). The EMR is stored, saved and accessed by the patient and approved physicians to facilitate treatment of the patent. The patient's medical health information may also be stored on an e-portal or patient portal that contains the patient's health information, including physician visits, discharge summaries, medications, immunizations, allergies, lab results, insurance information, contact information, educational materials and related personal health information. The collection of passive objective information is also utilized by the federal government and the private health insurance industry to establish benchmarks for quality outcomes, quality, efficiency and payment models. The EMR typically includes subjective information associated with the patient, typically generated from questionnaires answered by the patient. The questionnaires are the most commonly used outcome measure. Only some of the subjective questionnaires are validated and may be of reduced value based on patient inherent variability, truthfulness, expectations and the skillfulness of a patient to assess their own condition and function. Objective test result information such as height, weight, temperature, blood pressure, x-rays, range of motion, heart rate, respiratory rate, sleep, mental health, fall detection, blood glucose monitoring and other objective test results are typically gathered when the patient is at an appointment with the physician or with another referred medical professional. Objective test results are typically considered more reliable and consistent than the subjective questionnaire information and are preferably included in the patient's EMR and e-portal.

The preferred system and method consistently combines subjective and objecting measurement of the patient over a period of time, including pre-procedure, at medical appointments, between medical appointments, during procedures and post-operative. In combination with typical questionnaires, the preferred system incorporates real time tracking and smart technology to provide consistent objective testing information of the patient between appointments and procedures and following procedures.

Figure 8:
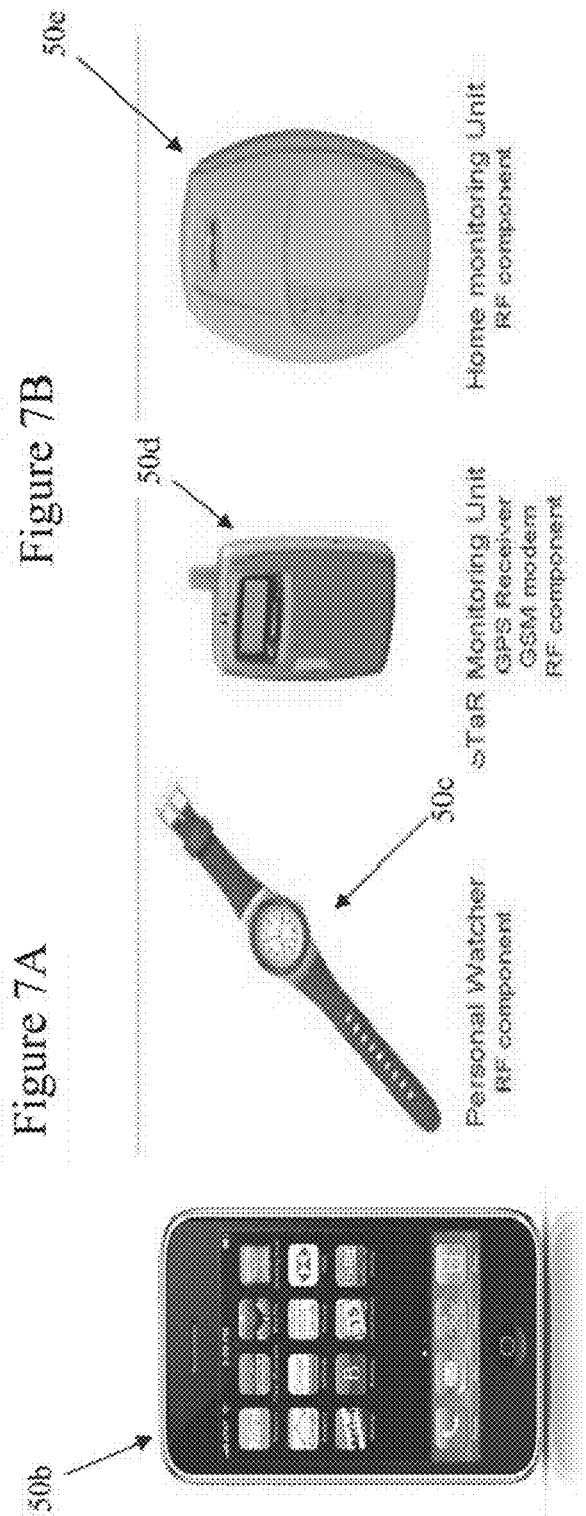
FIG. 8 is a rendering of several data collection tools that may be utilized with the system of FIG. 6.
Figure 9A:
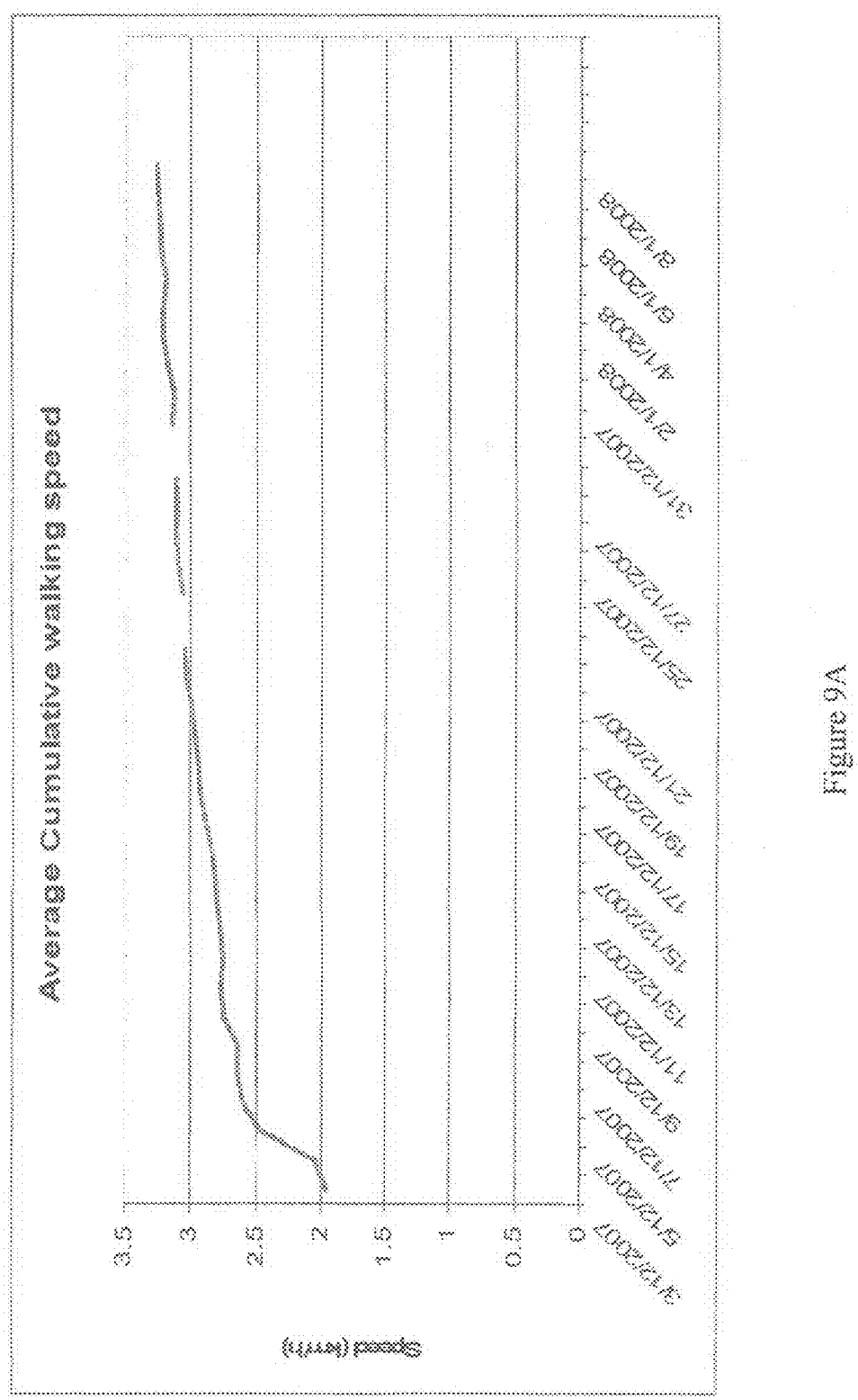
FIGS. 9A-9D, taken together, are graphical representations of objective walking data that may be collected utilizing the data collection tools of the system of FIG. 6.
Figure 9B:
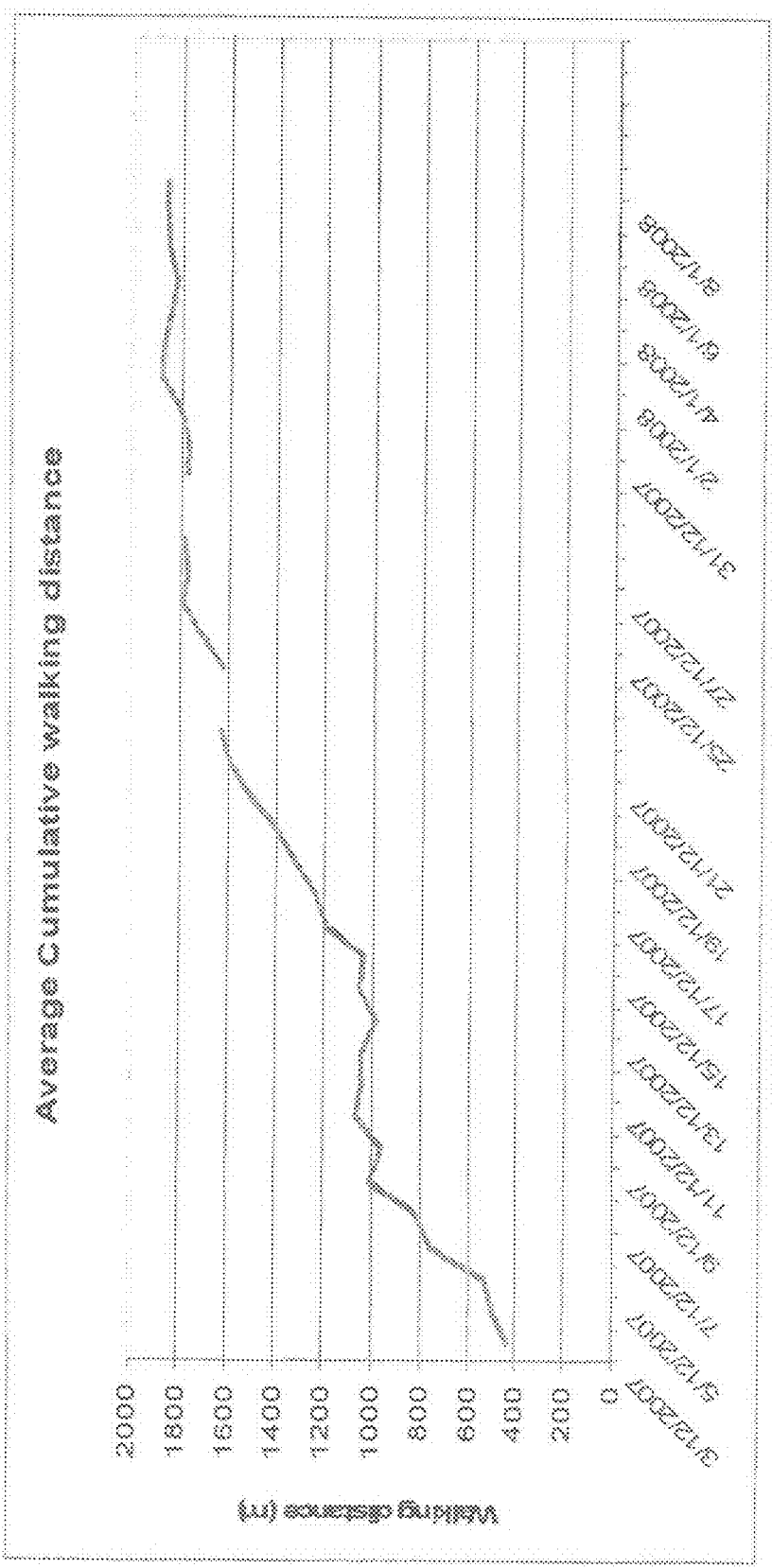
Figure 9C:
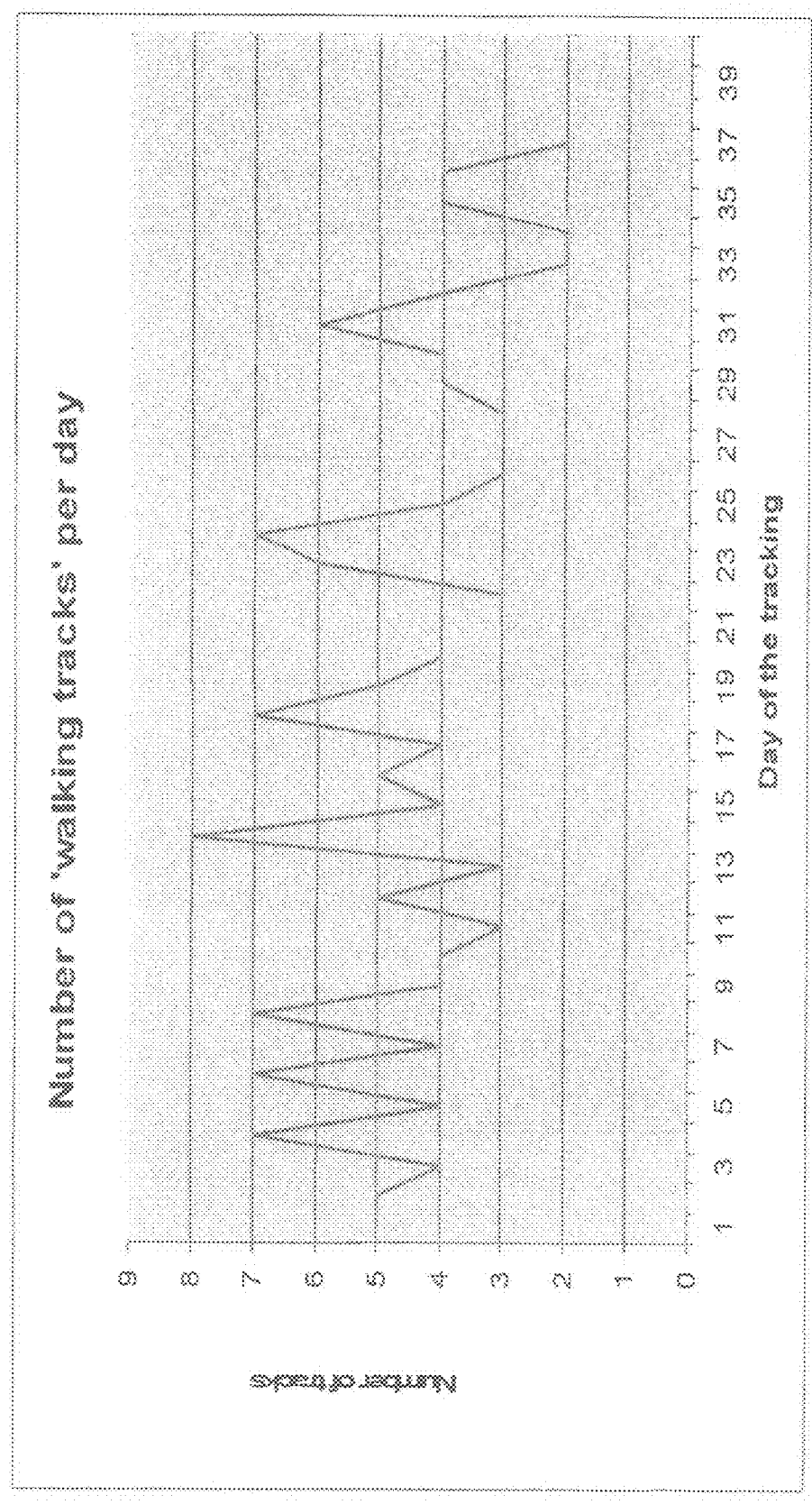
Figure 9D:
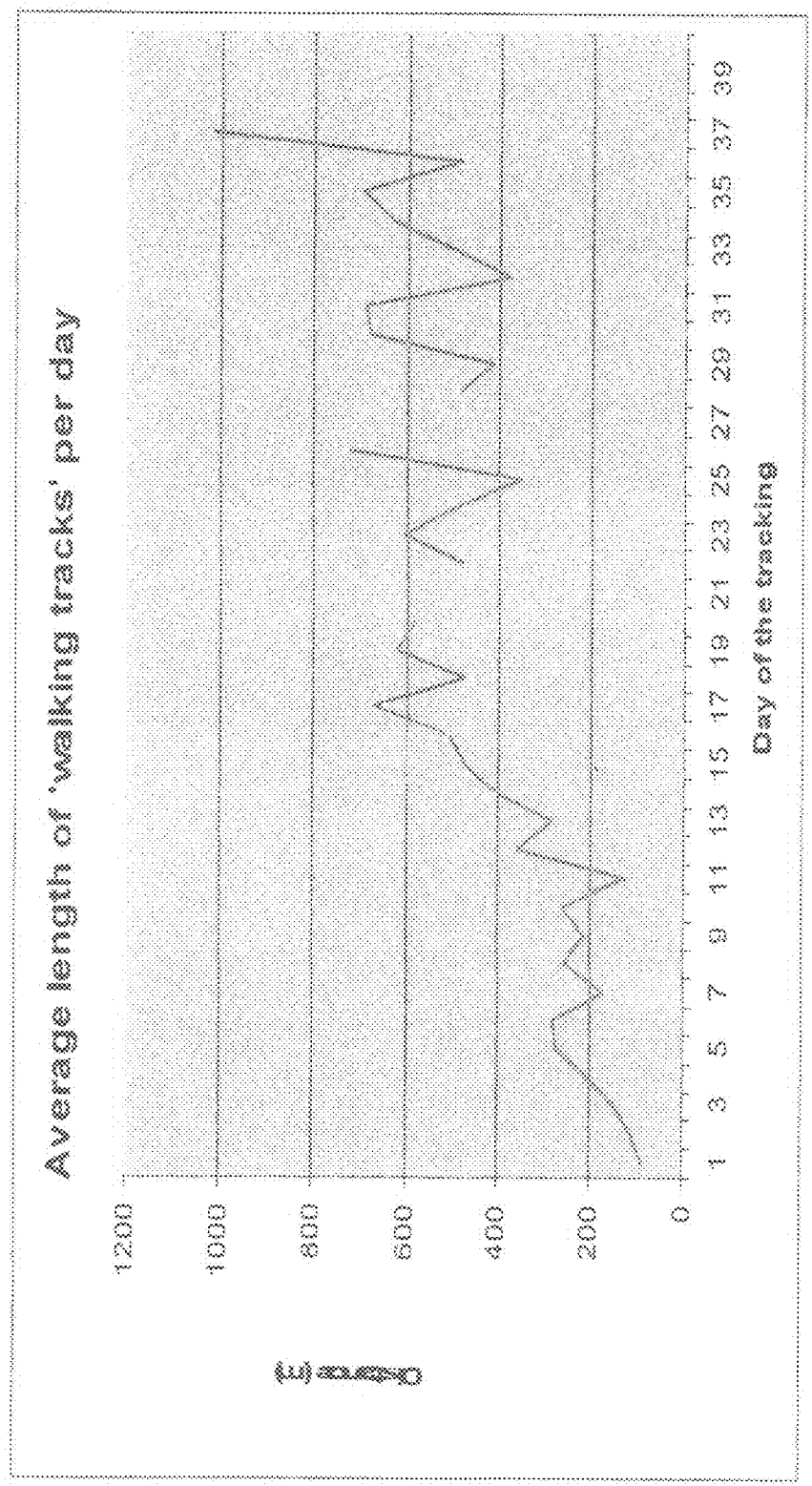

Referring to FIGS. 6-8, the preferred system utilizes data collection tools 50a, 50b, 50c, 50d, 50e (collectively, "50"), such as smart phones 50b, personal watches 50c with wireless communication capability, monitoring units 50d, for example, a STAR Monitoring Unit 50d with GPS receiver, GSM model and RF component, or customized sensor systems 50e, for example, a Home monitoring Unit RF component 50e, to consistently and constantly collect data regarding the patient. The data collection tools 50 may include sensor systems 12, a battery 19, specialized gauges 18, a transmitter 20 and a monitoring chip 30 in the preferred embodiment. The battery 19 preferably provides power to the data collection tool 50 and is rechargeable. The specialized gauges 18 may be comprised of a single gauge or sensor, such as a global positioning system ("GPS") sensor that tracks the patient's movements and mobility or the patient's immobility when they are sedentary of sleeping, but is not so limited. The specialized gauges 18 may be comprised of a plurality of gauges that acquire various objective information regarding the patient, such as location, movement, temperature, sleep patterns, and other related information that is preferably transmitted to a central server 40 and stored in the patient's EMR.

The GPS sensor is particularly preferred for the present system to collect data related to the patient's movements following an orthopedic procedure such as a knee or hip replacement or other orthopedic procedures to track the patient's movements while out of the presence of a medical professional or physical therapist or to track the patient's recommended rest or sleeping patterns based on lack of movement. The GPS sensor is preferred to track the consistency with which the patient is following physically therapy protocols, particularly exercises performed outside of the presence of the physical therapist or physician, and any improvements in their movements as a result of the physical therapy. Patients are preferably engaged with gamification to motivate the patient to provide quick subjective responses for completion of quality outcome surveys of various types. The information is preferably transmitted by the transmitter 20, which may be comprised of a wireless transmitter 20 that wirelessly transmits the information to the central server 40 or may alternatively be comprised of a hard-wired transmitter that is physically connected to a pathway for transmitting information to the central server 40. The data collection tools 50 may further include the monitoring chip 30 that is able to collect information related to the patient's external environment, such as temperature, humidity, presence of chemical compounds, sunlight levels, pH, vibration, conductivity and related environmental conditions. The data collection tools 50 may measure numerous patient activities including walking, eating, sleeping, shopping, sexual activity and other related activities. The data collection tools 50 may also be utilized to prompt subjective information from the patient, such as by providing a questionnaire to the patient following particular activities or at times when the patient is likely to provide such feedback.

The data collection tools 50 may be comprised of specialized tools or sensor assemblies that are secured to the patient or a device associated with a procedure conducted on the patient. For example, the preferred data collection tool 50 may be a specialized tool, sensor or transmitter attached to an implant that is implanted in the patient during an orthopedic procedure, may be attached to the patient near a surgical site of the orthopedic procedure or may be secured to bandages or coverings associated with the surgical site. Data collection tools 50 that are attached to implants could be configured such that the monitoring chip 30 detects the presence of infection, potentially enabling a surgeon to perform a procedure to limit infection, such as a polyethylene exchange instead of a two-stage revision. Data collection tools 50 connected to an implant may also be utilized to measure mechanical strain and loading forces to detect particular conditions, such as intra-articular conditions conducive to joint wear in vivo. Alternatively, the data collection tools 50 may be comprised of personal digital assistant ("PDA") devices, such as smartphones 50b, tablets, watches 50c, glasses or other personal items that incorporate sensors for use with the preferred system. The data collection tools 50 may also be comprised of specialized monitoring units that are provided to the patient by the physician or medical professional for limited time use during recovery from an orthopedic procedure or pre-operative and post-operative to a procedure, such as the STAR Monitoring Unit GPS Receiver GSM model and RF component 50d or the Home monitoring Unit RF component 50e.

The preferred data collection tools 50 are not limited to utilization with knee and hip joints and may be utilized with back braces to detect the amount of time the patient is wearing the brace, in splints, boots and casts to measure time spent in the device and adherence to weight-bearing prescriptions, associated with rehabilitation procedures, or associated with home therapy to track compliance with the therapy and associated with devices that treat pain to track patient activity or inactivity that triggers use of the paint treatment device or drug. The wearable data collection tools 50 of the preferred embodiment can combine kinematic, biometric and sleep data with patient-reported outcomes to provide a relatively precise understanding of patient outcomes, progress and condition.

The combination of the subjective and objective data collected utilizing the preferred system and method can also be utilized to develop patient risk models prior to conducting a procedure. The risk models may drive decisions related to the procedure, whether to conduct the procedure or to conduct an adapted procedure, the recovery plan following the procedure and related matters associated with the particular patient. The system is preferably able to produce high-risk flag that send automatic alerts to primary contacts based on an aggregation of the subjective and objective data collected from the patient. For example, an abnormally high temperature or fall followed by an extended period of inactivity may result in an automatic alert being sent to a family point of contact for the patient, to the patient's physician, to a patient manager who may be prompted to directly communicate with the patient, to the patient requesting response to a subjective questionnaire or other communication with the medical provider or other conditions wherein an automatic alert is appropriate.

Referring to FIG. 7B, the data collection tools 50 may comprise an epidermal electronics data acquisition tool 50*a*. The epidermal electronics data acquisition tool 50*a* is preferably attachable to the patient's skin, similar to a temporary tattoo, is preferably disposable and has the ability to track heart rate, hydration level, muscle movement, temperature, brain activity, oxygen saturation, blood glucose, strain, electrophysiologic sensing or related information. The epidermal electronics data acquisition tool 50*a* is preferably, but not limited to being, in communication with the central server 40 to communication this objective acquired data. In the preferred embodiment, the epidermal electronics data acquisition tool 50*a* is approximately seven to nine micrometers (7-9 μm) thick (0.007-0.009 mm, <0.0004"), approximately nine hundredths grams (0.09 g-0.003 oz.), can withstand physiologic strain of approximately thirty percent (30%) strain without detaching from the patient and is able to withstand the normal operating condition of the epidermal electronics data acquisition tool 50*a*. The epidermal electronics data acquisition tool 50*a* may also be configured without a battery 19 and may be powered by a piezoelectric device that converts motion of the patient's body to energy to power the epidermal electronics data acquisition tool 50*a*. The epidermal electronics data acquisition tool 50*a* preferably is wearable by the patient for at least twenty-four hours (24 hrs.) without degradation or skin irritation, but is not so limited and may be wearable for less or more time, but preferably more time in the preferred system. The epidermal electronics data acquisition tool 50*a* may be utilized as the data collection tool 50 for the system or may be utilized with one or more data acquisition tools 50, as is described herein. The data collection tool 50 may measure change in speed with accelerometer technology that is converted into velocity and position of the patient.

Referring to FIGS. 9A-9D, taken together, the preferred data collection tools 50 are able to acquire consistent walking and movement information from the patient, particularly post-operative walking or movement activity. FIGS. 9A-9D, taken together, provide examples of graphic displays of information the data collection tools 50 may acquire and transmit to the central server 40 for storage in the patient's EMR. The data collection tools 50 also preferably acquire movement information of the patient, such as car trips and other general travel of the patient. The trips may be analyzed by the physician, physical therapist or medical professional for duration of travel, stops during travel, reasons for stops, destinations and other related information. Depending on the acquired data or other information, the data collection tool 50 may prompt the user with subjective questionnaires based on the acquired data or collected information, such as questions related to why the patient is stopping at particular intervals during travel, where and why the patient is stopping, whether the travel is for business or pleasure and other related questionnaire prompts that can be answered by the patient directly on the data collection tool 50, such as on the smartphone 50*b* and securely transmitted to the central server 40. Such prompting and monitoring of the patient, even passively by the data collection tools 50, may improve patient compliance with physical activity recommendations by increased motivation, knowledge of monitoring and ability to track progress based on reviews of their EMR.

Referring to FIGS. 6, 7, 8, and 9A-9D, the data collection tools 50 may also be selectively placed and configured to target specific motions of the patient. In a preferred embodiment, the data collection tools 50 may be attached at or near a joint or multiple data collection tools 50 may be attached at different sides of the joint that undergoes an orthopedic procedure to collect data regarding specific motions at the joint, such as range of motion or speed of motion. The multiple data collection tools 50 may be positioned at different sides of the joint, such as above and below the knee on the leg to collect data regarding relative movement of the data collection tools 50 relative to each other that may provide information and data related to range of motion of the joint, potential twisting during such motion, speed of motion and other related information. For example, a first epidermal electronics data acquisition tool 50*a* may be placed above the knee joint and a second epidermal electronics data acquisition tool 50*a* may be placed below the knee and the relative positioning between the two may be monitored to detect movement of the joint during recovery. The first and second epidermal electronics data acquisition tools 50*a* may also be positioned on two sides of a shoulder joint to detect movement of the patient's shoulder and arm relative to the shoulder pre and post-operative to detect movements that aggravate the joint and can be utilized in combination with subjective questionnaires to prompt immediate feedback from the patient following movements, such as movements during physical therapy. Such information and data acquisition may be particularly preferred for analysis of physical therapy performed by the patient post-op during recover and comparison over time of any progress or regression of the patient. Such information and data acquisition may also be utilized to detect risky knee mechanics to limit or prevent ligament injuries, such as anterior cruciate ligament ("ACL") injuries. Similar devices and configurations could be utilized for spinal cord injury patients to monitor and detect improper movement techniques that may produce pressure sores. The spine information may be collected to placing a plurality of epidermal electronics data acquisition tools 50*a* along the patient's spine to acquire data related to relative movement of the tools 50*a* relative to each other and, therefore, movement of the patient's spine. The information may further be utilized to determine if the patient is performing particular physical therapy exercises incorrectly or is not participating in physical therapy, which may prompt messages or questionnaires to the patient regarding compliance with the prescribed therapy. The messages may include visual reminders regarding proper therapy motions, messages reminding the patient of frequency and therapy schedules, questionnaires regarding the patient's pain level or perceived well-being before during and after therapy and related messages and prompts. The patient may also have the ability to input real-time information to the data collection tools 50 regarding health utilization, pain perception, sleep patterns, movement and other related information.

The combined subjective and objective data and information collected from the data collection tools 50 and transmitted to the central server 40 may allow early detection of abnormal recovery from surgery, detection of greater than expected recovery from surgery or quicker recovery than expected, confirmation of as-expected recovery from surgery or related outcomes. The collection of data may permit delay of return appointments of the patient to a medical professional, thereby reducing medical costs and increasing patient convenience or may accelerate scheduling of an appointment with a medical professional if abnormalities are detected, thereby potentially reducing the probability of negative outcomes for the patient, such as emergency room visits, infection progression or related negative outcomes. The data collection tools 50 may also be configured to permit text, audio and/or visual communication between the patient and a medical professional, such as providing feedback to the patient regarding pain, correct technique for therapy exercises or other like questions or concerns. Communication through the data collection tools 50, such as through the smartphone 50b, provides potentially immediate feedback to the patient to remedy concerns and potentially enhance recovery. The collection of the data and storage in the patient's EMR further permits the physician or medical professional to provide a remote watch-dog function, detect complications, detect noncompliance with prescribed therapies, detect other pathologies and otherwise maintain access to patient progress or regression without requiring the physical presence of the patient with the physician or physical therapist. In addition, the physician or medical professional may be more prepared for face-to-face appointments or meetings with the patient based on pre-appointment analysis and consideration of the collected data from the data collection tools 50.

The data collected from the data collection tools 50 may be utilized to study healthy populations to generate norms, investigate pathologies impacting mobility and document the effect of treatments and best practices. The collected data may provide information related to the parameters that reflect best practices for recovery or best practices to accelerate recovery, when an abnormal recovery should be expected and which parameters (pre-op) predict undesirable outcomes so that the medical professional can make a determination regarding whether the patient is a candidate for a particular procedure, such as surgical intervention. The data collected form the data collection tools 50 is preferably comprised of a combination of objective data, such as movement, time, temperature, heart rate, blood pressure, respirations, ambulation, sleep duration and related objective data, and subjective data, such as pain levels, general health level, dizziness levels, scaled joint stiffness and related subjective data.

Communication between the central server 40, the patient, the physician and other individuals involved in the network is preferably through short message service ("SMS") communication protocol, but is not so limited and may be alternative messaging protocols, such as various alternate and secure messaging protocols or private portals. The SMS communication protocol, such as messages between the smartphones 50b of the patient and the physician is relatively seamless and easy for the participants to use.

The preferred system and method delivers an independent working unit that provides services to healthcare providers enabling them to track the level of activity that a patient demonstrates over a designated period of time and creates an objective tool to measure the outcome of orthopedic surgery and other medical interventions. The objective data is preferably combined with subjective questionnaires and information to provide an overall state of the patient for review by the medical professional. The preferred system and method preferably has the ability to remotely collect, analyze and report data for indoor and outdoor activity in the forms of outdoor mobility, such as time spent walking, walking speed, consistency of walking speed, walking terrain, location, walking claudicating and related forms of outdoor mobility, and motion, such as gait analysis, indoor levels of activity, including sitting, lying down, walking around the home and related motions. The data collection tools 50 are preferably configured to collect this data and may be installed on or provided to the patient, are readily utilized by medical professionals, may be maintained in their normal working environment and are supported by technical support who have the ability to troubleshoot technical problems with the data collection tools 50. The data collection tools 50 are also preferably able to communication with the central server 40 via direct connection through cable or land lines or wireless communications via cellular modems or wireless modems. The communications between the central server 40 and data collection tools 50 are also preferably secure to prevent loss or breach of the data.

In the preferred embodiment, data is collected via the data collection tools 50 for relatively long periods of time, such as months, if desired by the patient, physician or medical professional, without the need to download data. The data downloads are preferably commenced via wireless communications, during recharging of the battery 19, when convenient for the patient to connect to a hard wire or during medical appointments. The data may be monitored on a frequent basis, such as daily or in real-time, to determine patient compliance with prescriptions or the patient's general progress and recovery. The data, particularly data related to movement following orthopedic procedures, is collected in relatively high resolution of space (meters) and time (seconds). The relatively high space and time data collection resolution allows detailed and accurate information about the activities of the patient.

The preferred system and method may also be utilized for clinical studies to provide relatively accurate and frequent data regarding study patients. The preferred system and method may further be utilized to compare products, systems, protocols and treatments to proof the efficacy and superiority of particular products, systems, protocols and treatments.

The preferred system and method permits collection and reporting of medical procedure outcomes, preferably, but not limited to, orthopedic surgical outcomes. The system preferably evolves patient EMRs from document management to patient relationship management systems for educational materials for the patient, biometric device integration and patient reported outcomes. The system preferably provides evidence based medicine for utilization by patients, physicians and medical professionals. The preferred system may improve quality of life, expedite rehab, minimize use of skilled nursing facilities, automate tedious office tasks, reduce in-office visits (less out of pocket expenses & travel time for patient), control costs (bundled payments): pre-op processing and timing, procedure specific tasks and timing, ninety (90) day post-op visits with physicians and physical therapists, and long-term outcomes for the patient. Use the data from the preferred system may transform clinical care practices with respect to cost savings, outcomes and related measures. In the preferred method, the system asks patients questions, preferably via web and/or smartphone 50b to collect subjective data, provides physical therapy instruction & ask questions, preferably via electronic means, collects objective data via data collection tools 50 and provides physical therapy instructions to patients, preferably with visual instructions regarding motions and potentially with the ability to motion capture the patient performing the prescription that are transmitted to the central server 40 via the data collection tools 50. The preferred system has the benefit of providing evidence-base medicine and provides between-visit progress and compliance to the medical professional. These benefits have the ability to drive medical costs, including recovery and rehab, and are potentially beneficial for managing post-op cost of care.

Figure 10:
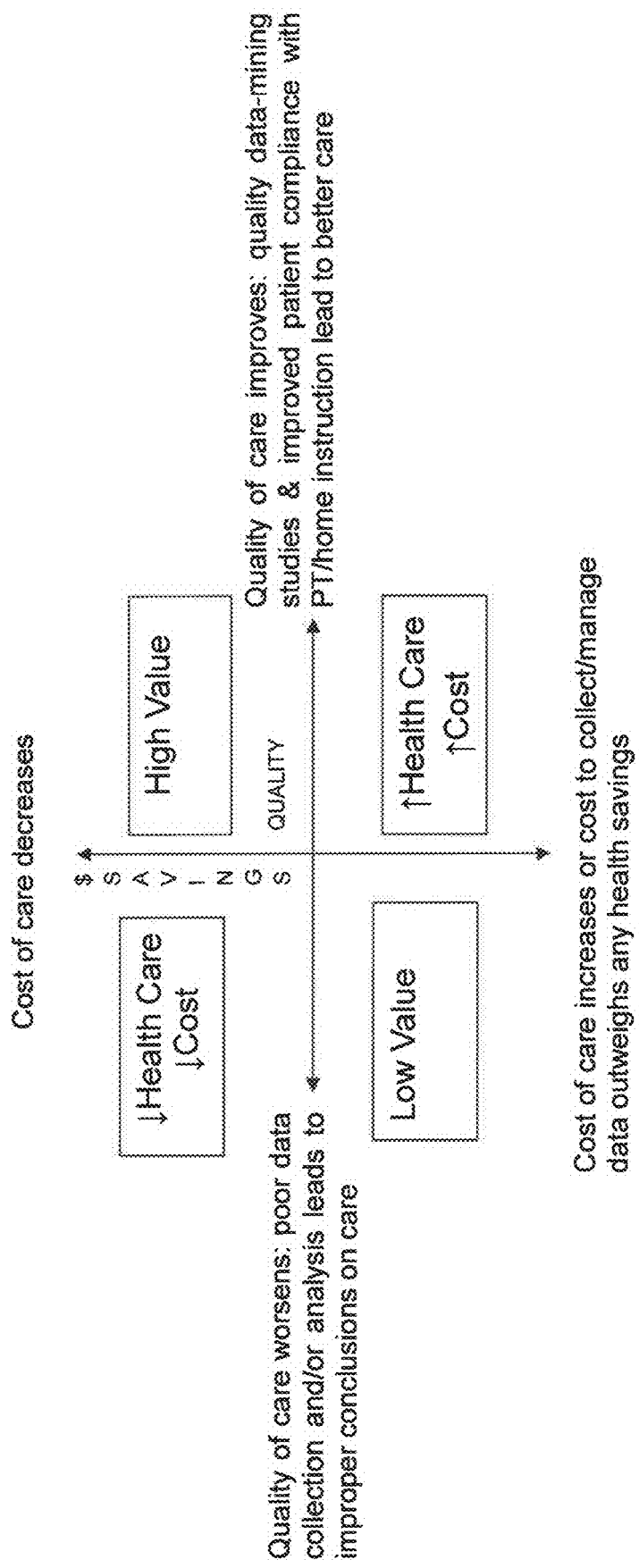
FIG. 10 is a graphical representation of a quality/cost value analysis related to the system of FIG. 6.

Referring to FIG. 10, the preferred system has the ability to reduce costs to implement new programs and translate findings of research driven clinical care. The preferred system may transform the current template of clinical studies that require the patient to return at specific time points into universally collected data that does not require constant and frequent patient meetings between or presence with a medical professional. The clinical studies may be conducted generally remotely, thereby decreasing inconvenience for study patients and freeing time for study professionals and coordinators. Clinical studies are able to utilize the preferred system's combined patient reported outcomes ("PROs"), generally via questionnaires with wearable devices and motion capture utilizing the data collection tools 50. The PROs may include questions related to condition-specific matters and quality of life. These portions of data may include information and data collected via paper, telephone and electronically based on the subjective answers of the patients. The subjective data is preferably combined and analyzed with the objective data from the data collection tools 50, which may include motion capture, activity monitors, biometrics (blood pressure, respiration rate, temperature, etc.), and range of motion and monitors of physical therapy progress. In finite studies, PROs & biometric devices effectively test specific hypotheses. The preferred system is able to scale & collect data universally in order to inform many ongoing studies.

The subjective data, which is typically collected at patient appointments or via questionnaires, provides a large source of baseline data. The baseline data permits creation of a profile for each provider and each type of appointment. Patients may then automatically deliver PROs for each visit. The subjective data may also be collected between visit via the collection tools 50, such as the smartphone 50b, by prompting the user to answer questions before, during and/or after activities, such as physical therapy.

The preferred data collection tools 50 have the ability to track general activity, including range of motion, provide feedback on progress for physicians and patients, and can be incorporated into existing physical therapy programs to improve the programs or track patient performance in the programs. For example, the data collection tools 50 may have the ability to provide video exercise instructions post-op. In addition, the data collection tools 50 have the ability to provide data to the central server 40 regarding compliance with the physical therapy program, the patient's ability to complete physical therapy exercises and track PROs. Patients can further directly message care providers through the data collection tools 50. The data collection tools 50, such as the smartphone 50b, preferably provide two-way communication for physical therapy and medical professionals and may be limited to a finite post-op time period, dependent on patient progress. The data collection tools 50 can provide a relatively comprehensive view of patient's post-op recovery and PROs can be collected at greater post-op periods when compared to current practices.

The data collection tools 50 are not limited to providing two-way communication, and may be limited to one-way communication, such as the epidermal electronics data acquisition tool 50b only transmitting collected data to the central server 40, the watch 50c only transmitting collected data to the central server 50 or the customized sensor system 50e only transmitting information to the patient from the physician or other medical professional. The communication may be both open-ended, wherein the patient and medical provider are able to write, voice record and/or orally communicate in real time, or closed-ended wherein only specific types of responses are permitted between the patient and the central server 40, such as responses to subjective questions from the patient to the central server 40. The data collection tools 50 may also be configured to limit certain types of communication between the patient and medical provider or central server 40 for specific time periods or until triggering events that unlock certain communications, for example, the smartphone 50b may be limited to transmission of collected data from the smartphone 50b to the central server 40 until the patient completes a particular post-operative subjective questionnaire for transmittal to the central server 40. Completion of such questionnaire may subsequently unlock the smartphone 50b for two-way communication between the medical provider and the patient. Such locking and unlocking of the communication may be utilized to incentivize the patient to comply with desired subjective data collection. The patient may also be incentivized to complete the relatively low compliance subjective questionnaires by gamification, wherein the patient may be provided with points other incentives for completing low compliance subjective questionnaires, for timely completing physical therapy prescriptions that are tracked using the data collection tools 50 or through comparison with similarly situated patients indicating the patient's progress in recovery in comparison to similarly situated patients. The preferred system may alternatively incentivize the patient to adhere to physical therapy, prescriptions, subjective data feedback or other related matters by providing positive feedback to patients who complete various tasks in a timely fashion. For example, the central server 40 may send positive messages to patient's who complete prescribed tasks, provide reminders of upcoming tasks indicating recovery progress, provide reminders of limited remaining duration of recovery, provide other post-operative instructions or otherwise provide positive feedback to the patient to encourage compliance with prescribed recovery protocols.

The collected data from the preferred system is also preferably utilized for comparative effectiveness reporting to the patient and the physician. The central server 40 is able to compare the individual patient's recovery data, including the subjective and objective data collected by the system, to industry and system specific benchmark data. The comparison is utilized by the system to determine and learn over time which factors and treatments work best for which patients and which pose the greatest benefits, harms or potential adverse events or reactions. The system transmits these comparisons to the patient and the physician to assist the patient and physician in making informed decisions to improve health care of the patient and of a similarly situated population of patients.

To summarize the Part 2 embodiment, a system is provided for tracking patient recovery following an orthopedic procedure conducted by a physician utilizing subjective data and objective data and considering the patient's electronic medical record. In one preferred embodiment, the system includes a central server and a data collection tool.

The central server is configured to receive the subjective and objective data and transmit messages to and from the patient and to and from the physician.

The data collection tool is associated with the patient and is configured to receive questionnaires from the central server and prompt the patient to provide answers to the questionnaires at a predetermined time following the orthopedic procedure, the answers comprising at least a portion of the subjective data, the data collection tool also configured to sense location data of the patient following the procedure, the location data comprising at least a portion of the objective data, the data collection tool configured to transmit the answers and the location data to the central server, the central server creating a risk profile of the patient based on the electronic medical records, the central server compiling the risk profile, the subjective data and the objective data and transmitting a series of physician appointments to the data collection tool based on the compilation.

The data collection tool may be selected from the group consisting of an epidermal electronics data acquisition tool, a smartphone, a watch, a monitoring unit and a customized sensor system.

The epidermal electronics data acquisition tool may have a thickness of approximately seven to nine micrometers and a weight of approximately nine hundredths grams.

The epidermal electronics data acquisition tool may include a location sensor and a wireless transmitter, the location sensor collecting objective data including periodic movements of the patient and the wireless transmitter transmitting the periodic movements to the central server.

The epidermal electronics data acquisition tool is configured for securing to the patient's skin, and the epidermal electronics data acquisition tool is configured to withstand physiologic strain of approximately thirty percent without detaching from the patient's skin.

The data collection tool may include a sensor system, specialized gauges, a battery, a monitoring chip and a transmitter.

The monitoring chip may be configured to collect objective data, including temperature, humidity and vibration.

The compilation of the risk profile, the subjective data and the objective data may result in transmission of a warning message from the central server to the physician suggesting immediate follow-up with the patient.

The warning message may be transmitted to the physician's smartphone.

The answers may be transmitted from the data collection tool to the central server via short message service protocol.

The central server may be configured to motivate the patient to complete the questionnaires through gamification.

End of Part 2

It will be appreciated by those skilled in the art that changes could be made to the embodiment described above without departing from the broad inventive concept thereof. It is understood, therefore, that this invention is not limited to the particular embodiment disclosed, but it is intended to cover modifications within the spirit and scope of the present invention as defined by the present disclosure.

What is claimed is:

1. A system for tracking patient recovery following an orthopedic procedure, wherein the system is configured receive from a physical sensor pre-procedural and post-procedural walking parameters of the patient, including steps taken, the system further being configured to communicate with an electronic medical record (EMR) data repository that includes EMR data for the patient undergoing the orthopedic procedure, the system further being configured to communicate with a database that is in electronic communication with the physical sensor and the EMR data repository, the database including: (i) patient demographic data obtained from the EMR data repository, (ii) comorbidities, (iii) pre-procedural walking parameters, including steps taken, the pre-procedural walking parameters being obtained from the physical sensor, and (iv) the orthopedic procedure that the patient is undergoing, the system comprising:

(a) a user interface device configured to temporally allow the patient to electronically communicate their pre-procedural and post-procedural pain level;

(b) a predictive model of the patient's post-procedural state for the orthopedic procedure, the predictive model using machine learning and being trained using training data sets;

(c) a statistical computing engine in communication with the user interface device and the database, and configured to use the items (i)-(iv) of the database and the pre-procedural pain level data collected by the user interface device to implement the predictive model of the patient's post-procedural state for the orthopedic procedure, the predictive model creating:
(i) a temporal trendline of post-procedural walking parameters, including steps taken, and
(ii) a temporal trendline of post-procedural pain level; and (d) a processor including a comparator configured to compare the patient's actual post-procedural state to the predictive model of the patient's post-procedural state, the processor being in electronic communication with the statistical computing engine, the physical sensor and the user interface device, the comparator of the processor:
(i) temporally comparing the post-procedural walking parameters, including steps taken, to the temporal trendline of post-procedural walking parameters, including steps taken,
(ii) temporally comparing the post-procedural pain level to the temporal trendline of post-procedural pain level, and
(iii) outputting the results of the comparison,
wherein the results of the comparison provide indicators regarding the patient's recovery status following the orthopedic procedure.

2. The system of claim 1 wherein the physical sensor that the system is configured receive pre-procedural and post-procedural walking parameters of the patient from, including steps taken, includes:
(i) a device worn by the patient and configured to collect movement/motion data, and
(ii) a mobile device including an application configured to receive data from the device.

3. The system of claim 2 wherein the device worn by the patient is an epidermally attached data device.

4. The system of claim 1 wherein the physical sensor that the system is configured receive pre-procedural and post-procedural walking parameters of the patient from, including steps taken, is a mobile device including:
(i) a movement/motion sensor, and
(ii) an application configured to receive data from the sensor.

5. The system of claim 1 wherein the patient demographic data includes one or more of patient age, BMI, and gender.

6. The system of claim 1 wherein the walking parameters further include one or more of walking velocity, gait cadence, and distance of continuous walking.

7. An automated method for tracking patient recovery following an orthopedic procedure, wherein an electronic medical record (EMR) data repository maintains EMR data for the patient undergoing the orthopedic procedure, and wherein patient pre-procedural and post-procedural walking parameters, including steps taken, are automatically collected using a physical sensor, and wherein a database that is in electronic communication with the physical sensor and the EMR data repository includes: (i) patient demographic data obtained from the EMR data repository, (ii) comorbidities, (iii) pre-procedural walking parameters, including steps taken, the pre-procedural walking parameters being obtained from the physical sensor, and (iv) the orthopedic procedure that the patient is undergoing, the method comprising:
  (a) electronically communicating the patient's pre-procedural and post-procedural pain level in a temporal manner to a statistical computing engine via a user interface device;
  (b) training a predictive model of the patient's post-procedural state for the orthopedic procedure using machine learning and training data sets;
  (c) using the statistical computing engine that is in communication with the user interface device and the database, and which is configured to use the items (i)-(iv) of the database and the pre-procedural pain level data collected by the user interface device to implement the predictive model of the patient's post-procedural state for the orthopedic procedure, the predictive model creating:
    (i) a temporal trendline of post-procedural walking parameters, including steps taken, and
    (ii) a temporal trendline of post-procedural pain level; and
  (d) comparing, using a processor having a comparator, the patient's actual post-procedural state to the predictive model of the patient's post-procedural state, the processor being in electronic communication with the statistical computing engine, the physical sensor and the user interface device, the comparator of the processor:
    (i) temporally comparing the post-procedural walking parameters, including steps taken, to the temporal trendline of post-procedural walking parameters, including steps taken,
    (ii) temporally comparing the post-procedural pain level to the temporal trendline of post-procedural pain level, and
    (iii) outputting the results of the comparison,
    wherein the results of the comparison provide indicators regarding the patient's recovery status following the orthopedic procedure.

8. The method of claim 7 wherein the physical sensor includes:
  (i) a device worn by the patient and configured to collect movement/motion data, and
  (ii) a mobile device including an application configured to receive data from the device.

9. The method of claim 8 wherein the device worn by the patient is an epidermally attached data device.

10. The method of claim 7 wherein the physical sensor is a mobile device including:
  (i) a movement/motion sensor, and
  (ii) an application configured to receive data from the sensor.

11. The method of claim 7 wherein the patient demographic data includes one or more of patient age, BMI, and gender.

12. The method of claim 7 wherein the walking parameters further include one or more of walking velocity, gait cadence, and distance of continuous walking.

13. The system of claim 1 wherein the user interface device employs one or more gamification techniques to encourage the patient to enter their pre-procedural and post-procedural pain level into the user interface device.

14. The system of claim 13 wherein one of the gamification techniques is to provide personalized prompts with feedback of recent input and progress status regarding the patient.

15. The system of claim 13 wherein one of the gamification techniques is to provide information that the patient values to incentivize engagement.

16. The method of claim 7 wherein the user interface device employs one or more gamification techniques to encourage the patient to enter their pre-procedural and post-procedural pain level into the user interface device.

17. The method of claim 16 wherein one of the gamification techniques is to provide personalized prompts with feedback of recent input and progress status regarding the patient.

18. The method of claim 16 wherein one of the gamification techniques is to provide information that the patient values to incentivize engagement.

19. The system of claim 1 wherein a post-surgical appointment schedule is provided to the patient following the orthopedic procedure, and wherein the results of the comparison are used to automatically modify one or more of dates and frequencies of appointments in the post-surgical appointment schedule.

20. The method of claim 7 wherein a post-surgical appointment schedule is provided to the patient following the orthopedic procedure, and wherein the method further comprises:
  (e) using the results of the comparison to automatically modify one or more of dates and frequencies of appointments in the post-surgical appointment schedule.

* * * * *